United States Patent
Ovchinnikov et al.

(10) Patent No.: US 10,314,953 B2
(45) Date of Patent: Jun. 11, 2019

(54) PARTIAL VENTING SYSTEM FOR OCCLUSION SURGE MITIGATION

(71) Applicant: Novartis AG, Basel (CH)

(72) Inventors: Mikhail Ovchinnikov, Dana Point, CA (US); Gary P. Sorensen, Mission Viejo, CA (US); Satish Yalamanchili, Irvine, CA (US)

(73) Assignee: Novartis AG, Basel (CH)

( * ) Notice: Subject to any disclaimer, the term of this patent is extended or adjusted under 35 U.S.C. 154(b) by 152 days.

(21) Appl. No.: 15/373,040

(22) Filed: Dec. 8, 2016

(65) Prior Publication Data

US 2017/0087283 A1    Mar. 30, 2017

Related U.S. Application Data

(63) Continuation of application No. 13/871,078, filed on Apr. 26, 2013, now Pat. No. 9,549,850.

(51) Int. Cl.
*A61M 1/00*    (2006.01)
*A61F 9/007*    (2006.01)

(52) U.S. Cl.
CPC ....... *A61M 1/0047* (2013.01); *A61F 9/00745* (2013.01); *A61F 9/00763* (2013.01); *A61M 1/0064* (2013.01); *A61M 2205/3337* (2013.01); *A61M 2210/0612* (2013.01)

(58) Field of Classification Search
CPC .............. A61M 1/0047; A61M 1/0064; A61F 9/00745; A61F 9/007636
See application file for complete search history.

(56) References Cited

U.S. PATENT DOCUMENTS

| | | |
|---|---|---|
| 3,558,100 A | 1/1971 | Hulsey |
| 4,944,261 A | 7/1990 | Coates |
| 8,876,751 B2 | 11/2014 | Dacquay et al. |
| (Continued) | | |

FOREIGN PATENT DOCUMENTS

| | | |
|---|---|---|
| CH | 692320 A5 | 5/2002 |
| JP | 2006-501419 A | 1/2006 |
| (Continued) | | |

OTHER PUBLICATIONS

Lueger, "Lexikon der Technik", Seite 199 und 200: Deutsche Verlags-Anstalt Stuttgart, Jan. 1, 1960 (T).
(Continued)

*Primary Examiner* — Edelmira Bosques (57) ABSTRACT

A surgical system comprises a hand piece, an irrigation conduit in fluid communication with the hand piece to carry fluid toward a surgical site, an aspiration conduit in fluid communication with the hand piece to carry fluid away from the surgical site, a pump interfacing with the aspiration conduit, the pump to create a vacuum pressure in the aspiration conduit to draw fluid through the aspiration conduit, a vacuum relief valve in fluid communication with the aspiration conduit to relieve the vacuum pressure in the aspiration conduit, a pressure sensor to detect a pressure associated with the surgical site, a controller in communication with the vacuum relief valve and the pressure sensor to control the vacuum relief valve to decrease the vacuum pressure in the aspiration conduit when the pressure detected by the pressure sensor is less than a first pressure threshold.

16 Claims, 6 Drawing Sheets

(56) References Cited

U.S. PATENT DOCUMENTS

| | | | |
|---|---|---|---|
| 2008/0018488 A1 | 1/2008 | Struck et al. | |
| 2008/0082040 A1* | 4/2008 | Kubler | A61M 1/0031 604/30 |
| 2009/0163853 A1* | 6/2009 | Cull | A61M 1/0031 604/35 |
| 2009/0270981 A1* | 10/2009 | Yavorski | A61M 1/106 623/3.21 |
| 2010/0185150 A1* | 7/2010 | Zacharias | A61M 1/0031 604/119 |
| 2010/0280434 A1 | 11/2010 | Raney et al. | |
| 2011/0092891 A1 | 4/2011 | Gerg et al. | |

FOREIGN PATENT DOCUMENTS

| | | |
|---|---|---|
| JP | 2010531676 A | 9/2010 |
| RU | 2333011 C1 | 9/2008 |
| WO | 2011075332 A1 | 6/2011 |
| WO | 2010135071 A1 | 11/2011 |

OTHER PUBLICATIONS

Auszug aus Wikipedia, Kugelhahn; www.wikipedia.org, May 16, 2017 (T).

* cited by examiner

PARTIAL VENTING SYSTEM FOR OCCLUSION SURGE MITIGATION

BACKGROUND

The present disclosure relates to phacoemulsification surgery and more particularly to a device that better regulates pressure experienced in the eye during cataract surgery.

The human eye functions to provide vision by transmitting light through a clear outer portion called the cornea, and focusing the image by way of a crystalline lens onto a retina. The quality of the focused image depends on many factors including the size and shape of the eye, and the transparency of the cornea and the lens. When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. A typical surgical hand piece suitable for phacoemulsification procedures consists of an ultrasonically driven phacoemulsification hand piece, an attached hollow cutting needle surrounded by an irrigating sleeve, and an electronic control console. The hand piece assembly is attached to the control console by an electric cable and flexible conduit. Through the electric cable, the console varies the power level transmitted by the hand piece to the attached cutting needle. The flexible conduit supplies irrigation fluid to the surgical site and draws aspiration fluid from the eye through the hand piece assembly.

The operative part in a typical hand piece is a centrally located, hollow resonating bar or horn directly attached to a set of piezoelectric crystals. The crystals supply the required ultrasonic vibration needed to drive both the horn and the attached cutting needle during phacoemulsification, and are controlled by the console. The crystal/horn assembly is suspended within the hollow body or shell of the hand piece by flexible mountings. The hand piece body terminates in a reduced diameter portion or nosecone at the body's distal end. Typically, the nosecone is externally threaded to accept the hollow irrigation sleeve, which surrounds most of the length of the cutting needle. Likewise, the horn bore is internally threaded at its distal end to receive the external threads of the cutting tip. The irrigation sleeve also has an internally threaded bore that is screwed onto the external threads of the nosecone. The cutting needle is adjusted so that its tip projects only a predetermined amount past the open end of the irrigating sleeve.

During the phacoemulsification procedure, the tip of the cutting needle and the end of the irrigation sleeve are inserted into the anterior segment of the eye through a small incision in the outer tissue of the eye. The surgeon brings the tip of the cutting needle into contact with the lens of the eye, so that the vibrating tip fragments the lens. The resulting fragments are aspirated out of the eye through the interior bore of the cutting needle, along with irrigation solution provided to the eye during the procedure, and into a vent reservoir.

Throughout the procedure, irrigating fluid is pumped into the eye, passing between the irrigation sleeve and the cutting needle and exiting into the eye at the tip of the irrigation sleeve and/or from one or more ports, or openings, cut into the irrigation sleeve near its end. This irrigating fluid is critical, as it prevents the collapse of the eye during the removal of the emulsified lens. The irrigating fluid also protects the eye tissues from the heat generated by the vibrating of the ultrasonic cutting needle. Furthermore, the irrigating fluid suspends the fragments of the emulsified lens for aspiration from the eye.

A common phenomenon during a phacoemulsification procedure arises from the varying flow rates that occur throughout the surgical procedure. Varying flow rates result in varying pressure losses in the irrigation fluid path from the irrigation fluid supply to the eye, thus causing changes in pressure in the anterior chamber (also referred to as Intra-Ocular Pressure or IOP.) Higher flow rates result in greater pressure losses and lower IOP. As IOP lowers, the operating space within the eye diminishes.

Another common complication during the phacoemulsification process arises from a blockage, or occlusion, of the aspirating needle. As the irrigation fluid and emulsified tissue is aspirated away from the interior of the eye through the hollow cutting needle, pieces of tissue that are larger than the diameter of the needle's bore may become clogged in the needle's tip. While the tip is clogged, vacuum pressure builds up within the tip. An occlusion break is when the clog is removed. The resulting drop in pressure in the anterior chamber in the eye when the clog is removed is known as post-occlusion surge. This post-occlusion surge can, in some cases, cause a relatively large quantity of fluid and tissue to be aspirated out of the eye too quickly, potentially causing the eye to collapse and/or causing the lens capsule to be torn.

Various techniques have been designed to reduce this surge. However, there remains a need for improved phacoemulsification devices that reduce post-occlusion surge as well as maintain a stable IOP throughout varying flow conditions. The present disclosure addresses one or more deficiencies in the prior art.

SUMMARY

In an exemplary aspect, the present disclosure is directed to a surgical system for treating an ocular condition. The system includes a hand piece, an irrigation conduit in fluid communication with the hand piece and configured to carry fluid toward a surgical site, and an aspiration conduit in fluid communication with the hand piece and configured to carry fluid away from the surgical site. The system also includes a pump that interfaces with the aspiration conduit and that is configured to create a vacuum pressure in the aspiration conduit to draw fluid through the aspiration conduit. The system includes a vacuum relief valve in fluid communication with the aspiration conduit and configured to relieve the vacuum pressure in the aspiration conduit. The system also includes a pressure sensor disposed and configured to detect a pressure associated with the surgical site and a controller in communication with the vacuum relief valve and the pressure sensor and configured to control the vacuum relief valve to decrease the vacuum pressure in the aspiration conduit when the pressure detected by the pressure sensor is less than a first pressure threshold. The controller may be configured to control the vacuum relief valve to stop the decrease of the vacuum pressure before the vacuum pressure reaches a vacuum level lower than −50 mmHg as measured at the eye.

In an aspect, the pressure sensor is located on the hand piece. In an aspect, the system includes a vent reservoir and a bypass conduit bypassing the pump and in fluid communication with the aspiration conduit and the vent reservoir, wherein the vacuum relief valve is located along the bypass conduit and wherein the vent reservoir is in fluid communication with the aspiration conduit.

In an exemplary aspect, the present disclosure is directed to a method of operating an aspiration system. The method includes directing a fluid through an aspiration conduit in fluid communication with a phacoemulsification hand piece, creating a vacuum pressure within the aspiration conduit using a pump interfacing with the aspiration conduit to draw an aspiration fluid from a surgical site and into the aspiration conduit, detecting with a pressure sensor a pressure associated with the surgical site, and relieving the vacuum pressure, using a vacuum relief valve, in the aspiration conduit when the pressure associated with the surgical site is less than a first pressure threshold, wherein relieving the vacuum pressure includes using the vacuum relief valve to maintain the vacuum pressure greater than about −50 mmHg.

In an exemplary aspect, the present disclosure is directed to a method of operating an aspiration system. The method includes creating a vacuum pressure within an aspiration conduit using a pump that interfaces with the aspiration conduit to draw a fluid from a surgical site and into the aspiration conduit, detecting with a pressure sensor a pressure associated with the surgical site, comparing the pressure detected by the pressure sensor associated with the surgical site to a first pressure threshold, and opening a vacuum relief valve to control the vacuum pressure in the aspiration conduit when the pressure associated with the surgical site is lower than the first pressure threshold to only partially vent the vacuum pressure while using the vacuum relief valve to maintain the vacuum pressure at a vacuum greater than about −50 mmHg.

In an aspect of any of the methods above, the pressure sensor is located on the hand piece. In an aspect, the vacuum relief valve is located on a bypass conduit that bypasses the pump and is in fluid communication with the aspiration conduit and a vent reservoir, and wherein the vent reservoir is in fluid communication with the aspiration conduit.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure.

DETAILED DESCRIPTION OF THE PREFERRED EMBODIMENTS

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately. For simplicity, in some instances the same reference numbers are used throughout the drawings to refer to the same or like parts.

The present disclosure relates generally to devices, systems, and methods for performing phacoemulsification procedures. During phacoemulsification, maintaining or quickly restoring IOP to a predetermined range can be critical to the success of the procedure. Early detection of a change to the IOP, such as a change due to an occlusion break, may provide sufficient time for a vacuum pressure within an aspiration line to be reduced, thereby reducing or preventing a post-occlusion surge and its undesirable effects. Vacuum pressure is a pressure lower than atmospheric pressure, and to increase the vacuum pressure is to further lower the pressure. Reducing or relieving the vacuum pressure is to bring the pressure closer to atmospheric pressure.

The devices, system, and methods disclosed herein include a hand piece having a pressure sensor to quickly detect occlusion breaks at the surgical site. In the exemplary embodiment disclosed herein, when an occlusion break is detected, a vacuum relief valve that is located on a pump bypass conduit opens to decrease the vacuum pressure (bring the vacuum pressure closer to atmospheric pressure) within the aspiration line, thereby reducing or preventing a post-occlusion surge. In one exemplary embodiment, after opening to decrease the vacuum pressure, the vacuum relief valve may be closed based on a triggering event, such as when pressure has sufficiently recovered. That is, after the vacuum relief valve is opened, an aspiration pressure sensor may detect whether the aspiration pressure has recovered and is greater than a threshold vacuum pressure. If it is, the vacuum relief valve is closed to decrease the vacuum pressure within the aspiration conduit. The system then resumes normal operation until another occlusion break is detected. In some aspects, the system is configured to only partially relieve the vacuum with the vacuum relief line so that the vacuum pressure changes from a higher vacuum pressure to reduced vacuum pressure (pressure closer to atmospheric).

Figure 1:
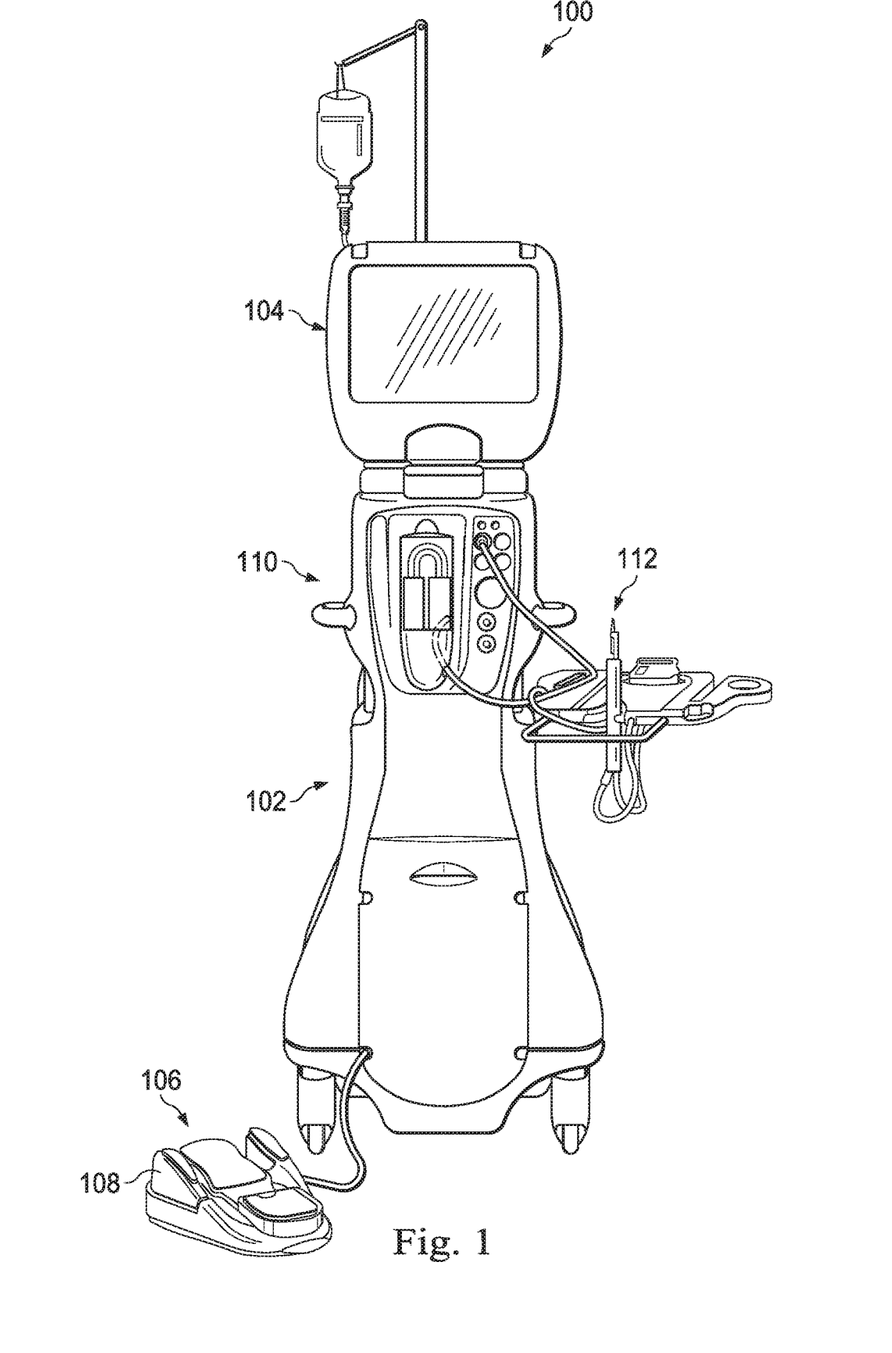
FIG. 1 is an illustration of an exemplary phacoemulsification surgical console according to one aspect of the present disclosure implementing the teachings and principles described herein.
Figure 2:
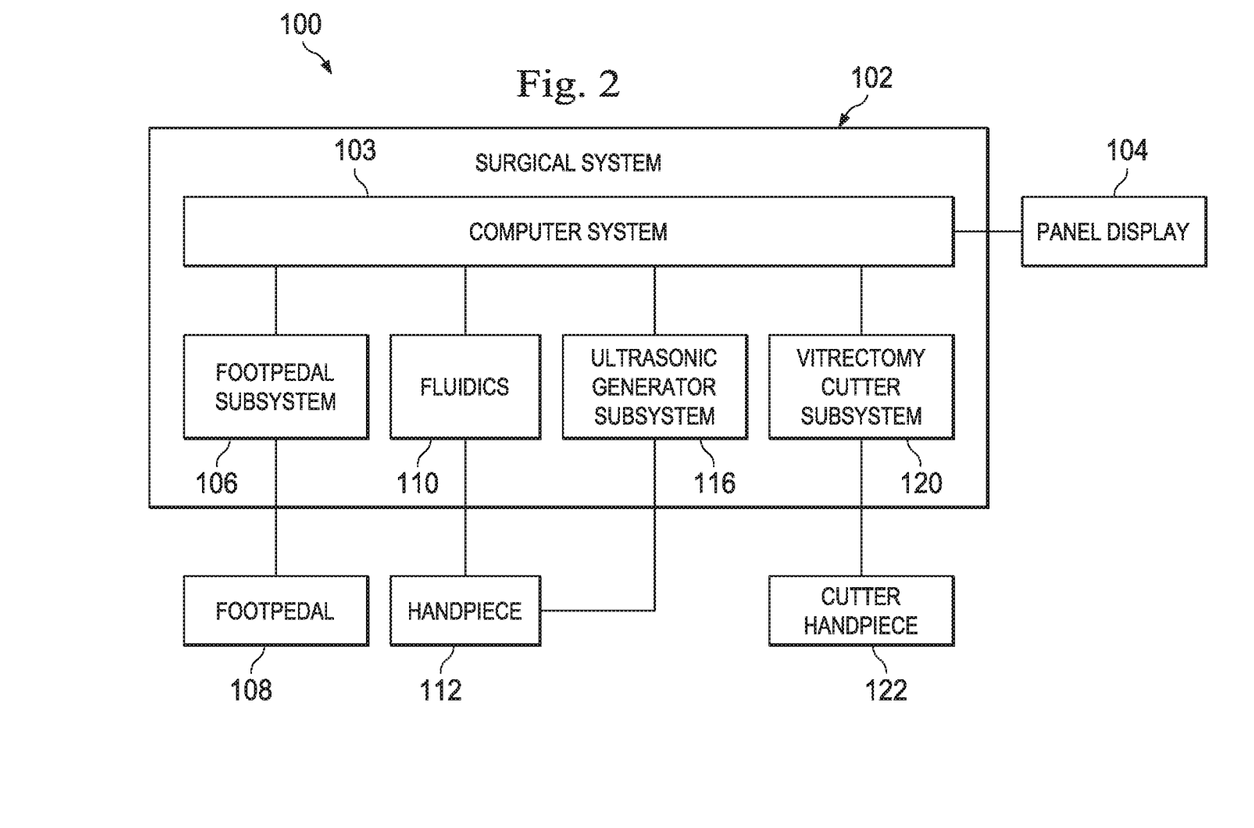
FIG. 2 is a block diagram of the phacoemulsification console of FIG. 1 showing various subsystems including a fluidics subsystem that drives aspiration according to the principles of the present disclosure.

FIG. 1 illustrates an exemplary emulsification surgical console, generally designated 100. FIG. 2 is a block diagram of the console 100 showing various subsystems that operate to perform a phacoemulsification procedure. The console 100 includes a base housing 102 with a computer unit 103 and an associated display screen 104 showing data relating to system operation and performance during an emulsification surgical procedure. The console 100 also includes a number of subsystems that are used together to perform a phacoemulsification surgical procedure. For example, the subsystems include one or more of a foot pedal subsystem 106 including, for example, a foot pedal 108, a fluidics subsystem 110 including a hand piece 112, an ultrasonic generator subsystem 116 that generates ultrasonic oscillation with the hand piece 112 with a cutting needle, and a pneumatic vitrectomy cutter subsystem 120 including a vitrectomy hand piece 122. These subsystems may overlap and cooperate to perform various aspects of the procedure.

Figure 3:
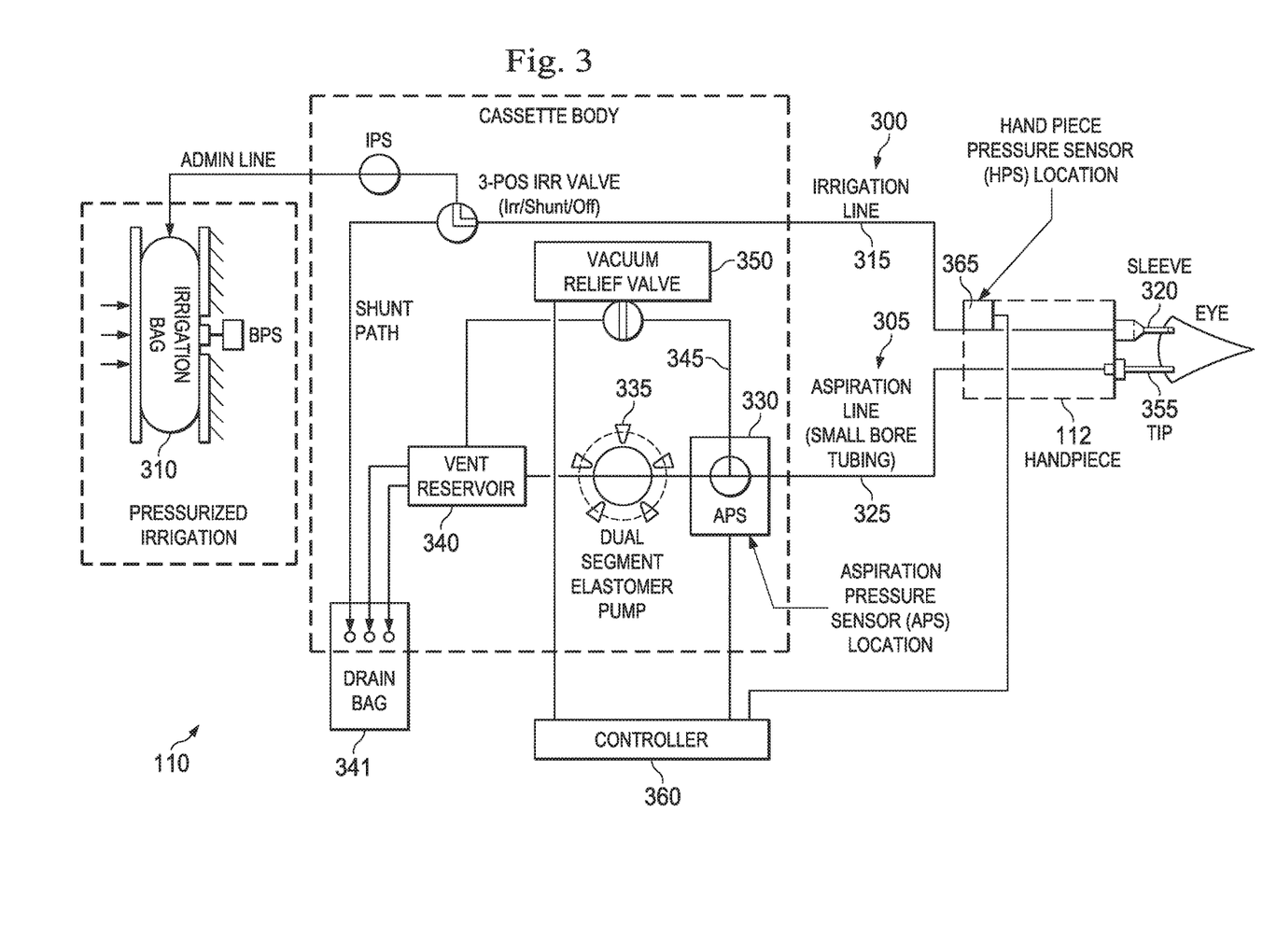
FIG. 3 is a schematic of an exemplary fluidics subsystem usable with the phacoemulsification surgical console of FIGS. 1 and 2 according to one aspect of the present disclosure.

FIG. 3 illustrates a schematic showing the fluidics subsystem 110 and the hand piece 112. The fluidics subsystem 110 includes an irrigation system 300 and an aspiration system 305 in fluid communication with the hand piece 112.

The irrigation system 300 includes an irrigation fluid source 310 and a flexible irrigation conduit 315 in fluid communication with a sleeve 320 located on the hand piece 112. The irrigation system 300 extends between the irrigation fluid source 310 and the hand piece 112, and carries fluid to the surgical site (labeled in FIG. 3 as an eye). In one example, the sterile fluid is a saline fluid, however, other fluids may be used. The irrigation fluid source 310 may be a mechanically pressurized fluid source such as, for example, a clamping pressure system as shown in FIG. 3. In an alternative embodiment, the irrigation fluid source 310 is a source suspended by an IV pole. Adjusting the source elevation may control the level of flow through the irrigation conduit 315 to the surgical site. Other fluid sources also are contemplated.

The aspiration system 305 includes an aspiration conduit 325 located in fluid communication with the hand piece 112, an aspiration sensor 330, a pump 335 interfacing with the aspiration conduit 325, and a vent reservoir 340. In some embodiments, the vent reservoir 340 may be a drain bag or an intersection of conduits. Other vent reservoirs also are contemplated. As can be seen, the aspiration system 305 extends from the surgical site (eye) to the vent reservoir 340 and ultimately on to a drainage or waste reservoir 341. The pump 335 creates a vacuum pressure within the aspiration conduit 325 between the pump 335 and the eye to draw the aspiration fluid from the surgical site and into the vent reservoir 340. A bypass conduit 345 is also in fluid communication with the aspiration line 325 and the vent reservoir 340 and bypasses the pump 335. A vacuum relief valve 350 is located along the bypass conduit 345 and controls the vacuum pressure within the aspiration conduit 325 by opening and closing. In the exemplary embodiment shown, the vacuum relief valve 350 is a variable vacuum relief valve. In one embodiment, the variable vacuum relief valve is a rotary valve. As described in greater detail below, the vacuum relief valve 350 may be controlled to open and close to decrease the effects of occlusion surge, so that IOP can be maintained or quickly restored to acceptable levels. For example, the vacuum relief valve 350 may be controlled to at least partially alleviate or reduce vacuum pressure in the aspiration conduit 325. The vacuum relief valve 350 may be fully opened or partially opened to reduce the vacuum pressure in the aspiration conduit 325. The vacuum relief valve 350 may be fully closed or partially closed to increase the vacuum pressure (increase the difference between the pressure and the atmospheric pressure, bringing the pressure away from atmospheric pressure) in the aspiration conduit 325. However, as the vacuum relief valve is the process of closing, the vacuum pressure may still continue to decrease. That is, when the vacuum relief valve is closed, the vacuum pressure increases (moves away from atmospheric pressure), and during the process of closing the vacuum pressure can decrease (moves toward atmospheric pressure).

Upon opening of the vacuum relief valve 350, the vacuum pressure within the aspiration conduit 325 draws a fluid from the vent reservoir 340 into the bypass conduit 345. In one embodiment, the opening of the vacuum relief valve 350 reduces the vacuum pressure within the aspiration conduit 325. In another embodiment, the opening of the vacuum relief valve 350 maintains the vacuum pressure within the aspiration conduit 325 or slows the rate of increase of the vacuum pressure within the aspiration conduit 325. Therefore, opening the vacuum relief valve 350 controls the vacuum pressure by reducing the vacuum pressure, by maintaining the vacuum pressure, or by slowing the rate of increase of the vacuum pressure. Upon closing of the vacuum relief valve 350, the vacuum pressure continues to decrease. However, due to the closure of the pressure relief valve 350, the vacuum pressure within the aspiration conduit 325 can be maintained within a desired vacuum pressure range, which is described below. As indicated above, in some embodiments, the aspiration system 305, including the aspiration conduit 325, is in fluid communication with the cutting tip 355 of the hand piece 112 and is used to aspirate fluid and emulsified particles through the tip 355 and into the aspiration system 305 during the surgical procedure.

The fluidics subsystem 110 also includes a controller 360, which is in communication with a pressure sensor 365 located within the hand piece 112, the aspiration pressure sensor 330, and the vacuum relief valve 350. The controller 360 may include a processor and memory that may include an executable program for operating the vacuum relief valve 350 and or detecting information received from the sensors 365 and 330. In one embodiment, the controller 360 is a PID controller configured to control the valve 350 to mitigate pressure deviations, such as occlusion surge.

In one example, the controller 360 may include one or more pre-established pressure thresholds establishing desired pressure limits. When the measured or detected pressure passes beyond these pre-established thresholds, the controller 360 controls the valve to restore the pressure to a desired level. In one example, the thresholds are a function of vacuum pressure setting, flow rate, and intraocular pressure (IOP). The controller 360 may include a first pressure threshold relating to the irrigation pressure as a representation of ocular pressure and a second pressure threshold relating to a minimum operating pressure or minimum vacuum pressure. Similar thresholds may be included for a flow rate and a vacuum setting. For example, there may be a desired vacuum pressure range within the aspiration conduit that represents the range of vacuum pressures at which the system operates under normal conditions (without occlusions or occlusion breaks). These thresholds may be input by an operator or may be preset and stored during manufacturing.

The controller 360 also receives information from the pressure sensor 365 and aspiration pressure sensor 330. The controller 360 is configured to control the operation of the vacuum relief valve 350 based on the information received from the pressure sensor 365 and the aspiration pressure sensor 330. The pressure sensor 365 is located on the hand piece 112 close to the surgical site and in some embodiments, is disposed less than 12 inches from the surgical site.

From its location in the hand piece, the pressure sensor 365 detects a fluid pressure associated with the surgical site. Its proximity to the eye enables quick detection of changes in pressure (as may occur during an occlusion break) and allows for real-time surge suppression. Some embodiments detect pressure changes as quickly as within 50 milliseconds of an occlusion break. Such a fast response time may enable the controller 360 to quickly provide a response to pressure deviations before IOP is overly negatively affected.

In the exemplary embodiment shown, the pressure sensor 365 is disposed in the hand piece 112 along the irrigation conduit 315. Although shown at the proximal end of the hand piece 112, in other embodiments, it is disposed at the distal end and may be disposed proximate the sleeve 320. In one embodiment, the pressure sensor 365 is an irrigation pressure sensor 365 located along the irrigation conduit 315 within the hand piece 112. The irrigation pressure sensor detects the irrigation pressure within the irrigation conduit 315. In another embodiment, the pressure sensor 365 is located in the hand piece 112 and is in fluid communication with the surgical site through a communication element other than the irrigation conduit 315. For example, the pressure sensor 365 may be disposed within its own separate tube or probe in communication with the surgical site. In one such embodiment, the separate tube or probe is independent of the hand piece 112 but permits the pressure sensor 365 to be disposed within close range of the surgical site. In alternative embodiments, it may be disposed within the sleeve 320 or elsewhere on the hand piece 112.

In operation, irrigation fluid is provided to the surgical site through the irrigation conduit 315. In the exemplary embodiment shown, the sensor 365 is located along the irrigation conduit 315 to detect the irrigation pressure within the irrigation conduit 315. The controller 360 continuously monitors the pressure using the sensor 365. If the irrigation pressure drops lower than the first pressure threshold stored in the controller, as may occur during an occlusion break, the controller 360 opens the vacuum relief valve 350 to reduce the vacuum pressure within the aspiration conduit 325 to reduce or prevent a post-occlusion surge. When the aspiration pressure sensor 330 detects that the aspiration pressure is greater than the second pressure threshold, then the controller 360 closes the vacuum relief valve 350 to control the rate of increase of the pressure within the aspiration conduit 325, and allows for the aspiration system to continue with normal operations after a period of time passes. That is, once the system detects that the aspiration pressure is greater than the second pressure threshold, the vacuum relief valve starts closing and during the process of closing, the vacuum pressure continues to decrease (moves closer to atmospheric pressure) albeit the rate is changed. Once the vacuum relief valve is closed, the vacuum pressure may increase (move away from atmospheric pressure) or remain the same (if that is the normal operating condition vacuum pressure).

In some embodiments, the controller 360 vents the system by opening the vacuum relief valve 350 such that the vacuum level returns to ±50% of the normal operating condition vacuum level without complete loss of followability. For example, in some embodiments, the normal operating condition vacuum level is a vacuum greater than about −50 mmHg, and the vacuum level is controlled so as to not rise above −50 mmHg near the pump that creates vacuum in the aspiration line, as detected for example by the aspiration sensor. In some embodiments, the vacuum level is controlled so as to prevent the pressure from rising about −100 mmHg as detected by the aspiration sensor. In other embodiments, the vacuum level is controlled so as to prevent the pressure from rising above −150 mmHg. Yet other thresholds are contemplated. In some embodiments, the second pressure threshold is set to ensure the pressure does not rise over the pressures identified above.

Accordingly, in some embodiments, the system only partially vents the vacuum pressure so that the pressure does not rise to atmospheric pressure, and the vacuum pressure is maintained. As such, the controller may use the vacuum relief valve to control the vacuum pressure so that it decreases from an excessively high vacuum to a lower suitable vacuum. As used herein the terms "partial venting" or "partially vent" vacuum pressure are intended to mean that the vacuum pressure decreases toward atmospheric pressure, but is controlled to prevent the vacuum pressure from reaching atmospheric pressure.

In some embodiments, the amount and rate of opening of the vacuum relief valve 350 correlates to the difference between the aspiration pressure (measured via the aspiration pressure sensor) and the pressure set point threshold. That is, if the pressure deviation is minimal, the vacuum relief valve 350 is only partially opened to a minimally open setting, and if the pressure deviation is larger, the vacuum relief valve is opened a larger amount. Because of this, the system does not degrade the followability or the holding power. Instead, the valve control may provide control and stability for surge mitigation that may not be achieved by fully opening and closing the valve in response to deviation beyond a threshold.

In some exemplary embodiments, the vacuum relief valve 350 is controlled to close without a measurement taken from the aspiration sensor 330. For example, in some exemplary embodiments, the vacuum relief valve 350 reduces the vacuum pressure within the aspiration conduit 325 by rapidly pulsing between an open position and a closed position for a predetermined period of time. For example, the valve may rapidly open and close as directed by the controller 360, in order to alleviate the vacuum pressure created by the occlusion. Such an embodiment may not include the sensor 330 because the controller 360 closes the valve after a preset length of time instead of being based on a detected pressure reading. No aspiration sensor 330 is necessary due to the assumption that the post-occlusion surge will be prevented based on a pulsing vacuum relief valve 350 for a predetermined period of time. In other embodiments, the vacuum relief valve 350 may be controlled to open a single time for a predetermined time to alleviate the vacuum pressure. For example, the vacuum relief valve 350 may open, for example only, for 0.040 seconds and then be configured to automatically close. In some embodiments, the vacuum relief valve 350 may open around 0.025 seconds, and in other embodiments, for time periods less than 0.025 seconds. These time periods are exemplary only and other time periods are contemplated. In one aspect, the predetermined time that the vacuum relief valve 350 may be opened and the degree that the valve may be opened may be selected based on the level of vacuum pressure detected or the amount of deviation from the threshold, in the manner described above. Such an embodiment may also wait a period of time before continuing with normal operation to allow for the system to recover from the occlusion break.

Figure 4:
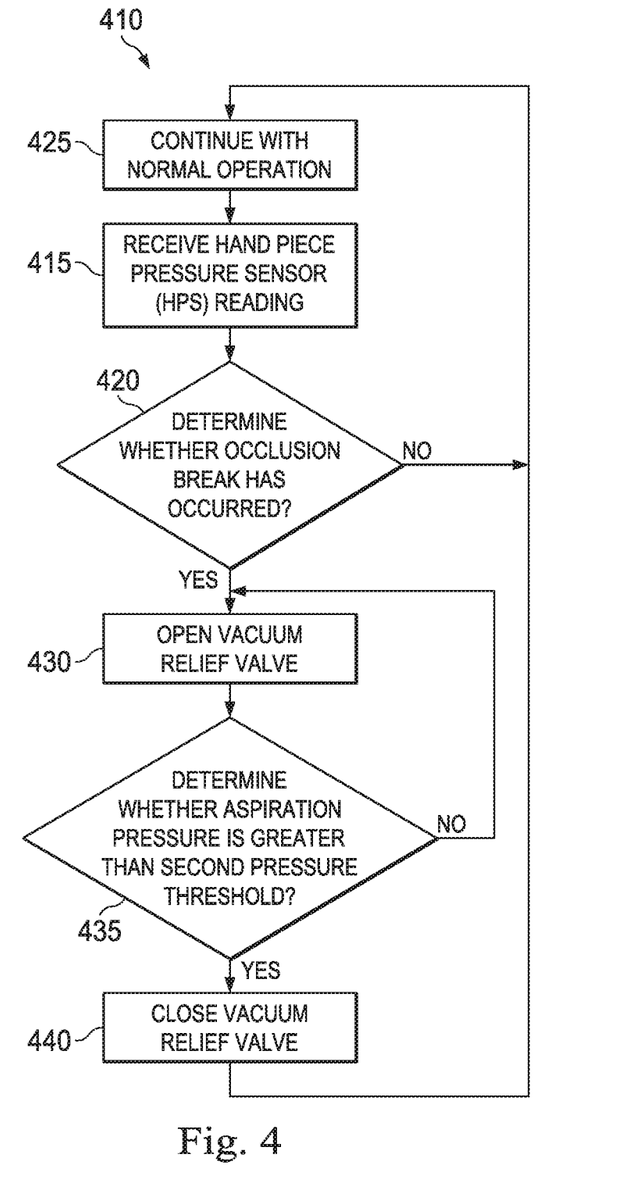
FIG. 4 is flow chart illustrating a method of operating the system of FIG. 3, according to an embodiment consistent with the principles of the present disclosure.

FIG. 4 illustrates an exemplary method 410 for operating the system. At step 415, the pressure sensor 365 detects a pressure associated with the surgical site and communicates the detected pressure to the controller 360. Accordingly, the controller receives the detected pressure value. For example, and as described above, the pressure sensor 365 may be an irrigation pressure sensor detecting irrigation pressure using the irrigation conduit pressure or may be a sensor located on the sleeve 320 and detecting pressure near the surgical site.

At step 420, the controller 360 determines whether an occlusion break has occurred. This may include comparing the pressure measured by the pressure sensor 365 to a predetermined pressure threshold, or first pressure threshold, to determine whether the pressure has dropped below the first pressure threshold. When the pressure drops below the first pressure threshold, the controller 360 determines that an occlusion break has occurred. However, if the pressure remains above or at the first pressure threshold, then the controller 360 determines that an occlusion break has not occurred. If an occlusion break has not occurred, normal operation continues at step 425, followed by the step 415. If an occlusion break has occurred, then the next step is step 430.

At the step 430, the controller 360 operates the vacuum relief valve 350 to open, or at least partially open, in order to reduce or relieve the vacuum pressure in the aspiration conduit 325. Upon opening or the at least partial opening of the vacuum relief valve 350, the vacuum pressure within the aspiration conduit 325 draws a fluid from the vent reservoir into the bypass conduit 345. This movement of the fluid from the vent reservoir into the bypass conduit 345 alleviates or reduces the amount of vacuum pressure within the aspiration conduit 325. As described above, in some embodiments, opening of the vacuum relief valve 350 maintains the vacuum pressure or increases the rate of decrease of the vacuum pressure. As described above, in some embodiments, the controller 360 regulates the amount that the valve is opened based on the difference between the detected pressure and the pressure threshold. Accordingly, in these embodiments, the controller 360 may determine a difference between the actual detected pressure and the first threshold and then control the vacuum relief valve based on the difference. In one embodiment, the controller includes a table that corresponds to valve settings with the amount of deviation from the threshold. During operation, the controller 360 may open the valve 350 a certain amount based on data found in the table.

At step 435, the controller 360 determines whether the aspiration pressure is greater than a predetermined vacuum pressure or second pressure threshold. It does this by detecting the aspiration pressure with the aspiration pressure sensor 330 located along the aspiration conduit 325. The controller 360 is in communication with the aspiration pressure sensor 330 and may continuously receive information from it. The controller 360 compares the information received from the aspiration pressure 330 with the second pressure threshold. If the vacuum pressure is less than or equal to the second pressure threshold, then the vacuum pressure is below the minimum operating pressure and the next step is to return to the step 430, at which the vacuum relief valve 350 remains open.

If the pressure is greater than the predetermined vacuum pressure, then at step 440, the vacuum relief valve 350 is closed and a period of time passes to allow for the system to recover after the occlusion break. In some aspects, the second pressure threshold is a vacuum pressure threshold and the system is arranged so that the vacuum relief valve is controlled to always maintain a particular vacuum within the system. After closure of the vacuum relief valve 350, the continuous operation of the pump will maintain the vacuum pressure within the aspiration conduit 325 within the desired vacuum pressure range. The next step is the step 425, which is to continue with normal operation. Using this method, occlusion breaks are detected and the vacuum pressure is controlled to reduce or prevent a post-occlusion break surge. Because of this, the IOP during surgery may be maintained within a desired range, and fluctuations in IOP are relatively stable, thereby reducing the potential of increased turbulence and endothelial cell damage.

Figure 5:
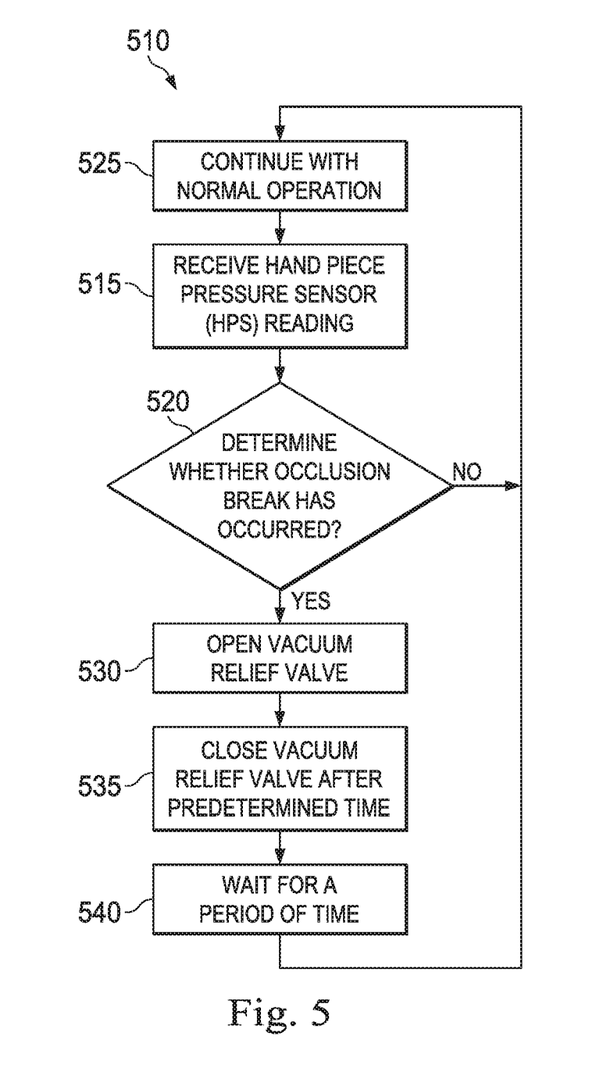
FIG. 5 is a flow chart illustrating a method of operating the system of FIG. 3, according to an embodiment consistent with the principles of the present disclosure.

In an alternative embodiment, as illustrated in FIG. 5, a method of operating the system is generally referred to by the reference numeral 510. Steps 515, 520, 525, and 530 are substantially similar to the steps 415, 420, 425 and 430 of the method 410, respectively, and therefore will not be discussed in detail. In FIG. 5 at step 535 of the method 510, after the vacuum relief valve is opened at the step 530, the vacuum relief valve is closed after a predetermined time. At a step 540, the system waits for a period of time before continuing with normal operation at the step 525. Normal operation is resumed after waiting a period of time to allow for the system to recover or normalize after the occlusion break.

Figure 6:
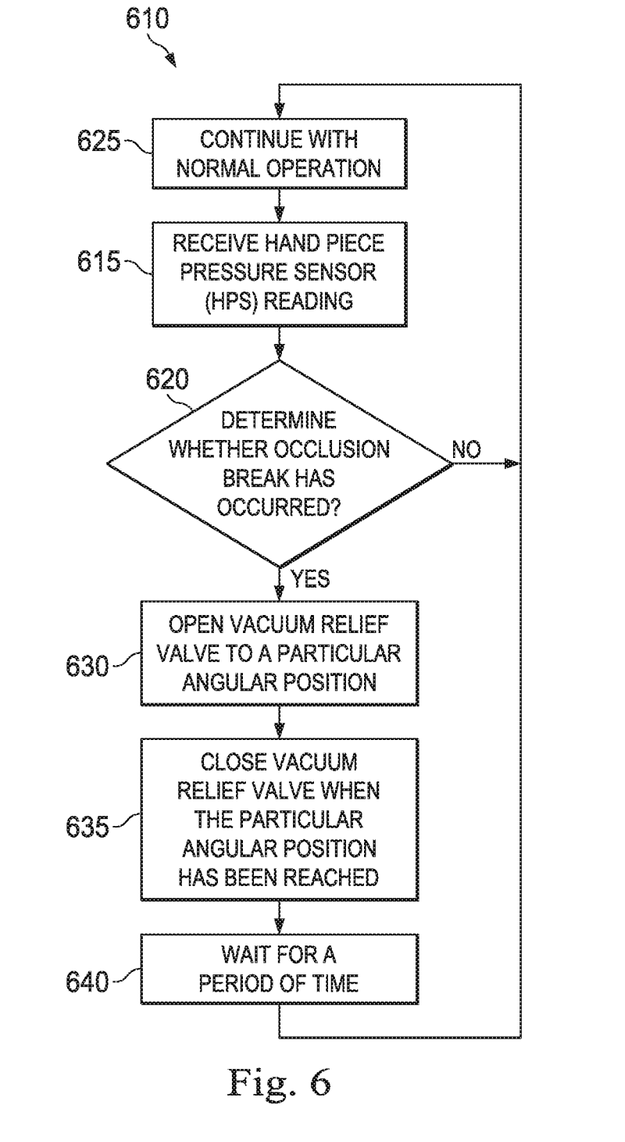
FIG. 6 is a flow chart illustrating a method of operating the system of FIG. 3, according to an embodiment consistent with the principles of the present disclosure.

In another alternative embodiment, as illustrated in FIG. 6, a method of operating the system is generally referred to by the reference numeral 610. Steps 615, 620, 625, and 640 are substantially similar to the steps 515, 520, 525 and 540 of the method 510, respectively, and therefore will not be discussed in detail. As will be understood from the following paragraphs, the method of FIG. 6 uses a position-based operation in place of the time-based operation discussed above with reference to FIG. 5.

The method of FIG. 6 may be implemented when the vacuum relief valve 350 of FIG. 3 is a rotary valve that opens to a particular angular position. In this embodiment, the controller 360 receives feedback indicating the amount that the valve is opened. When the vacuum relief valve 350 reaches a predetermined angular setting, the controller 360 closes it.

Referring to FIG. 6, at step 630, the controller 360 opens the vacuum relief valve 630 to a particular angular position when the controller 360 determines that an occlusion break has occurred. In some examples, the particular angular position is an angular position of less than about 45 degrees, and in some exemples, less than about 30 degrees. Accordingly, in some embodiments, the controller 360 sends a particular position command to the vacuum relief valve 350. At a step 635, the controller 360 controls the vacuum relief valve 350 to close the vacuum relief valve. This may occur when the controller 360 determines that the valve 350 is at the particular angular position. In some embodiments, the angular position may be selected on-the-fly based on the measured pressures to compensate for the different amounts of deviations.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure

What is claimed is:
1. A surgical system comprising:
   a hand piece;
   an aspiration conduit in fluid communication with the hand piece and configured to carry fluid away from a surgical site;

a pump interfacing with the aspiration conduit, the pump configured to create a vacuum pressure in the aspiration conduit to draw fluid through the aspiration conduit;

a vacuum relief valve in fluid communication with the aspiration conduit and configured to relieve the vacuum pressure in the aspiration conduit;

a first pressure sensor disposed and configured to detect a pressure associated with the surgical site;

a second pressure sensor located along the aspiration conduit, the second pressure sensor configured to monitor an aspiration pressure within the aspiration conduit;

a vent reservoir and a bypass conduit bypassing the pump and in fluid communication with the aspiration conduit and the vent reservoir, wherein the vacuum relief valve is located along the bypass conduit, and wherein the vent reservoir is in fluid communication with the aspiration conduit; and a controller having a first pressure threshold and a second pressure threshold stored therein and being in communication with the vacuum relief valve, the first pressure sensor, and the second pressure sensor, the controller being configured to control the vacuum relief valve to open the vacuum relief valve to decrease the vacuum pressure in the aspiration conduit when the pressure detected by the first pressure sensor is less than the first pressure threshold, and the controller being configured to control the vacuum relief valve to close the vacuum relief valve, wherein a period of time that the vacuum relief valve is opened is correlated to a difference between the first pressure threshold and the pressure detected by the second pressure sensor.

2. The system of claim 1, wherein the first pressure sensor is located on the hand piece.

3. The system of claim 1 further comprising
an irrigation conduit in fluid communication with the hand piece and configured to carry irrigation fluid toward a surgical site.

4. The system of claim 3 wherein the first pressure sensor is an irrigation conduit pressure sensor located along the irrigation conduit to detect an irrigation pressure within the irrigation conduit.

5. The system of claim 1, wherein the vacuum relief valve is configured to allow a vent reservoir fluid to enter the bypass conduit when the vacuum relief valve decreases the vacuum pressure in the aspiration conduit.

6. The system of claim 1, wherein the second pressure sensor is located between the pump and a tip coupled to the hand piece.

7. The system of claim 1, wherein the first pressure sensor is disposed less than about 12 inches from a tip coupled to the hand piece.

8. The system of claim 1 wherein the vacuum relief valve is controlled to partially open to an angular position of less than 45 degrees.

9. The system of claim 1 wherein the vacuum relief valve is controlled to partially open to an angular position of less than 30 degrees.

10. A method of operating an aspiration system, comprising:

directing a fluid through an aspiration conduit in fluid communication with a hand piece;

creating a vacuum pressure within the aspiration conduit using a pump interfacing with the aspiration conduit to draw an aspiration fluid from a surgical site and into the aspiration conduit;

detecting with a first pressure sensor a pressure associated with the surgical site;

detecting an aspiration pressure with a second pressure sensor located along the aspiration conduit; and decreasing the vacuum pressure in the aspiration conduit by controlling a vacuum relief valve such that the vacuum relief valve is opened to vent the vacuum pressure when the pressure associated with the surgical site is less than a first pressure threshold, and controlling the vacuum relief valve such that the vacuum relief valve is closed when the aspiration pressure is greater than a second pressure threshold, wherein a duration that the vacuum relief valve is opened is correlated to a difference between the first pressure threshold and the aspiration pressure wherein the vacuum relief valve is located on a bypass conduit that bypasses the pump and is in fluid communication with the aspiration conduit and a vent reservoir, and wherein the vent reservoir is in fluid communication with the aspiration conduit.

11. The method of claim 10, wherein the first pressure sensor is located on the hand piece.

12. The method of claim 10, further comprising:
directing a fluid through an irrigation conduit in fluid communication with the hand piece; wherein the first pressure sensor is an irrigation pressure sensor located along the irrigation conduit detecting an irrigation conduit pressure.

13. The method of claim 10, further comprising:
controlling the vacuum relief valve with a controller, wherein the controller is connected to the first pressure sensor and the second pressure sensor and the controller is configured to receive information from the first pressure sensor and the second pressure sensor.

14. The method of claim 10, further comprising:
controlling the vacuum relief valve with a controller that opens the vacuum relief valve to a particular angular position and that closes the vacuum relief valve when the particular angular position is reached.

15. The method of claim 14 wherein the vacuum relief valve is controlled to partially open to an angular position of less than 45 degrees.

16. The method of claim 14 wherein the vacuum relief valve is controlled to partially open to an angular position of less than 30 degrees.

* * * * *